United States Patent [19]

Koerner

[11] Patent Number: 4,640,334
[45] Date of Patent: Feb. 3, 1987

[54] APPARATUS FOR CASTING MATERIALS FOR FALSE TEETH

[76] Inventor: Rudi Koerner, Elisabethenstrasse 41, D-7080 Aalen-Unterkochen, Fed. Rep. of Germany

[21] Appl. No.: 804,667

[22] Filed: Dec. 3, 1985

[30] Foreign Application Priority Data

Dec. 13, 1984 [DE] Fed. Rep. of Germany ....... 3445424

[51] Int. Cl.$^4$ .................... A61C 13/20; B22D 13/00; B22D 13/10
[52] U.S. Cl. .................................. 164/287; 164/289; 164/292
[58] Field of Search ......... 164/287, 289, 292, DIG. 4, 164/114

[56] References Cited

U.S. PATENT DOCUMENTS

| | | | |
|---|---|---|---|
| 1,639,253 | 8/1927 | Ayers | 164/287 |
| 2,009,489 | 7/1935 | Fritzsche | 164/287 X |
| 2,637,079 | 5/1953 | Kemppe | 164/287 X |
| 2,778,075 | 1/1957 | Huppert | 164/287 X |
| 4,510,987 | 4/1985 | Collot | 164/114 X |

Primary Examiner—Nicholas P. Godici
Assistant Examiner—J. Reed Batten, Jr.
Attorney, Agent, or Firm—Hayes, Davis & Soloway

[57] ABSTRACT

A melt receptacle (4) together with a muffle (5) attached thereto by a connector is situated on a centrifugal arm (2) of a centrifugal device, which arm rotates during the casting operation. On a common structural unit (8) are situated a preheater furnace (1) and the connector (9,13) in a manner to allow, respectively, for the conveyance of the muffle (5) from the preheater furnace and the fastening thereto for which connector there can be used a manipulator arm (12) which carries out only one shifting movement in one plane and engages the muffle (5).

11 Claims, 4 Drawing Figures

APPARATUS FOR CASTING MATERIALS FOR FALSE TEETH

The invention concerns an apparatus for casting materials for false teeth, especially gold, from a melt receptacle into a muffle preheated in a preheater furnace, wherein the melt receptacle, together with the muffle attached thereto by a connecting means, is situated in a centrifugal arm that rotates during the casting operation.

A muffle in which is disposed a cavity with the negative mold serves for making false teeth, for instance, out of gold. The gold, for instance, is brought into the melt receptacle for fusing by electric heating. The melt receptacle is situated on a centrifugal arm that is set to rotate for casting the gold. The muffle is preheated in a preheater furnace and is removed with tongs from the preheater furnace and connected with the melt receptacle after the gold has reached the melting point. Rotation of the melt receptacle then follows whereby the molten gold flows into the externally attached muffle and fills up the negative mold in the muffle as a result of centrifugal force.

Filling the muffle by using pressure instead of with the aid of the centrifugal force is also known already for this. In this case the muffle comes into tight contact with the melt receptacle which is an enclosed space. If compressed air is now introduced into this space, the molten gold is expelled from the melt receptacle into the muffle.

However, the processes known already have as disadvantages the facts that they are relatively time-consuming and require several manipulations by operators. Thus, for instance, the preheated muffle has to be withdrawn from the furnace with tongs. Another problem is in the casting itself. If it is not carried out with precision, time-consuming and thus expensive refinishing operations are needed.

Therefore, this invention is directed to the problem of providing an apparatus for casting materials for false teeth that is easier to operate and by which a more precise cast is also produced.

According to the invention this problem is solved by situating on a common structural unit the preheater furnace and the connecting means sufficiently close to each other than an actuatable manipulator arm for conveying the muffle and fastening it to the connecting means carries out only one shifting movement in one plane.

While hitherto the preheater furnace stood in no precise spatial relationship to the centrifugal device with the centrifugal arm, said two parts are now situated on a common structural unit and aligned with respect to each other in a manner such that the muffle is removed from the preheater furnace in a simple manner by a manipulator arm and can be connected to the melt receptacle by the connecting means.

When the connecting means and the preheater furnace are on the same level or on the same plane, a shifting of the manipulator arm is needed only in one plane, and thus the assembly can be kept relatively simple. This requires only that bearing surface in the preheater furnace be substantially at the same height as the connecting means. In this manner the manipulator arm is secured to the centrifugal arm and is actuable via a pneumatic cylinder.

It is possible to carry out, for instance, a vacuum-pressure casting by this arrangement. Better casting results can be obtained thereby, since by means of a previous evacuation the molten mass to be introduced does not have to compress the air that would otherwise be present. In this manner the casting is substantially more precise and refinishing operations can be reduced to a minimum.

To facilitate the operation and for quicker preparation of the tooth molds, it is advantageous to have a supply cartridge for false teeth material that has been cut to size arranged in the interior of the centrifugal arm.

Where formerly a measured amount of material for only one false tooth was available in the melt receptacle, there is now used according to the invention a supply cartridge into which several measured amounts are placed. In this manner several casting operations can be carried out consecutively.

The construction of the supply cartridge is optional. Thus, it is possible to use, for instance, a rotary cartridge having chambers with discharged dies distributed over the periphery.

In a combined centrifugal/die-casting process it is required only that the supply cartridge be in the interior of the centrifugal arm. In this case the only consideration is that it be of easy access after being filled. A lid in the housing of the centrifugal arm, for instance, can serve this purpose. The same applies to the melt receptacle.

Instead of a supply cartridge situated in the interior of the centrigual arm, it is also possible to make the melt receptacle replaceable. In this embodiment a cartridge having several melt receptacles in each of which there is already the corresponding amount of material to be fused is placed outside the centrifugal arm on a stationary part. To change—after a fusing operation—a new melt receptacle is introduced from the outside into the centrifugal arm where the heating device can heat it. The old melt receptacle is then simultaneously discharged or ejected.

The manipulator arm can be secured to the centrifugal arm and moved by a pneumatic cylinder.

In the development according to the invention it is possible to dispose a pneumatic cylinder for horizontally moving the manipulator arm on the centrifugal arm and another pneumatic cylinder on a pick-off device for the muffle. This arrangement is relatively simple and thus of reasonable cost.

The pick-off device can be constructed in various ways. Thus, it can be, for instance, a sort of tongs having two clamping levers between which the pneumatic cylinder is situated. The pneumatic cylinder will here have a double action in general for simplicity and thus both clamping levers move synchronously in respect to the central plane between them.

The clamping levers can here be provided with retaining members that interact with reciprocal members disposed on the muffle to be conveyed.

It is likewise possible to arrange the retaining members and the reciprocal members in different manners.

A simple and very effective conveying connection consists in having the retaining members comprise clamping jaws and the reciprocal members lugs adapted to the outer contour of the clamping jaws on the peripheral wall of the muffle. The clamping jaws are built as segments of an arc, and the reciprocal members are constructed as corresponding concave segments. The front sides of concave segments can optionally have a stop radially spaced from the muffle in order to firmly hold the muffle during the centrifugal operation. In this configuration the pick-off device with the two clamping levers simultaneously provides for a tight connection with the melt receptacle. All that is needed for this to come about is that the corresponding parts to be built stable enough that the strong centrifugal forces which occur can be reliably absorbed.

Another very advantageous embodiment of the invention comprises an insert into the preheater furnace having at different heights bearing surfaces for the muffles in a manner such that longitudinal axes of all the muffles be at the same level for the conveyance of muffles of different diameters.

In this manner it is possible to work freely with muffles of different diameters or different sizes while the manipulator arm remains always at the same level and therefore can be of simple construction.

It is also advantageous to have the bearing surfaces rest on an arc of circle having its center at least approximately in the area of the axis of rotation of the centrifugal arm.

In this manner, it is possible to have several muffles situated next to each other in the furnace. These muffles are shaped to correspond with the longitudinal axis of the centrifugal arm with the manipulator arm secured thereon and thus can be removed from the preheater furnace by a simple rectilinear movement.

Herebelow is fundamentally described in detail with reference to the drawing an embodiment of the invention from which additional features of the invention result.

Figure 1:
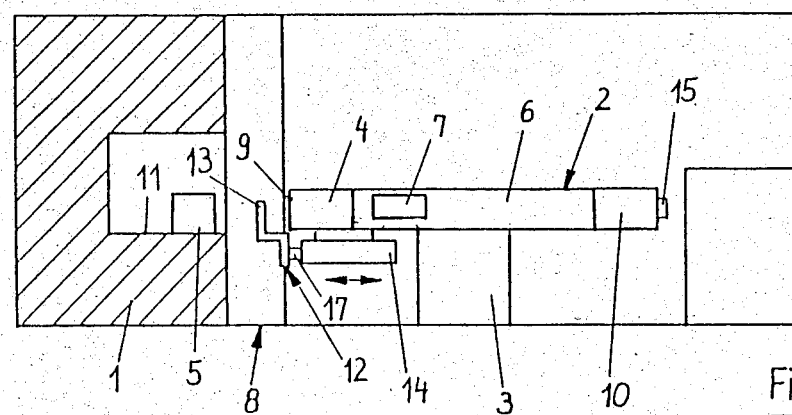
FIG. 1 is a side view of the apparatus according to FIG. 2.

The main component parts of an apparatus for casting materials for false teeth are generally known, for which reason they will be described only briefly herebelow. This applies specifically to a preheater furnace 1, a centrifugal arm 2 having a drive mechanism 3 and a melt receptacle 4.

The preheater furnace 1 serves to heat muffles 5, which have in the interior a hollow mold for crowns, bridges and the like.

The melt receptacle 4 consists in general of a carbon crucible heated by an electric resistance heater. Inside the carbon crucible is the material such as gold which is to be fused into the false tooth. The centrifugal arm 2 is constructed to include a tightly closed case, the melt receptacle 4 being in the interior 6 thereof. Also is disposed a supply cartridge in the interior 6 of the centrifugal arm 2. The supply cartridge 7 is a rotary cartridge having several chambers distributed on the periphery with discharged dies which introduce the gold to be fused for the casting operation into the melt receptacle 4.

The preheater furnace 1 and the centrifugal arm 2 with the drive mechanism 3 are situated in a common structural unit 8. One end of the centrifugal arm 2 is provided with a connecting means 9 while the other end has a counterweight 10 for balancing the weight.

Figure 3:
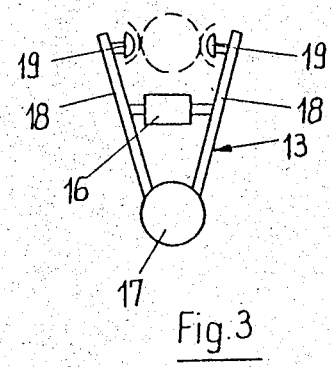
FIG. 3 is an enlarged view of the pick-off device.

As can be seen from FIG. 1, the bearing surface 11 of the preheater furnace 1 is at the same height as the connecting means 9. A manipulator arm 12 with a pick-off device 13 is situated at the end of the conveyor arm 2 on which is also the melt receptacle 4. A pneumatic cylinder 14 serves to actuate the manipulator arm 12. By actuating the penumatic cylinder 14, which can be centrally secured beneath the centrifugal arm 2, the manipulator arm 12 can be moved in horizontal direction by the piston rod 17 of the pneumatic cylinder 14 and by a further actuation of the pick-off device 13 via a second pneumatic cylinder 16, (see FIG. 3), a muffle 5 in the preheater furnace 1 can be removed and attached to the melt receptacle 4 (see FIG. 1). In this case the pick-off device 13 simultaneously serves also as connecting means 9. The operation of the pneumatic cylinders can be double or simple. In cylinders of simple operation the restoring force is produced by springs instead of compressed air. Commercially available cylinders can be used for said purposes.

Due to the strong centrifugal forces that occur, it may be advantageous to have the pneumatic cylinder 14 secured to the end of the centifugal arm opposite to the end having the melt receptacle 4. In this manner no force that pulls the piston away from the cylinder acts upon the piston of the cylinder during rotation.

The pick-off device comprises two clamping levers 18 between which is situated the pneumatic cylinder 16. The pneumatic cylinder 16 has two functions, that is, it is provided with two pistons and thus synchronously moves both clamping levers 18. At the proximal end both clamping levers 18 are flexibly connected with the forward end of the piston rod 17, while each distal end of the two clamping levers 18 is provided with a retaining member 19. As it can be seen from FIG. 3, both retaining members are constructed as clamping jaws having a convex surface. In order for the muffles 5 to be conveyed, they must have accurately disposed reciprocal members 20, which when the clamping jaws 19 are used, are lugs situated on the outer periphery of the muffle 5. Said lugs 20 are on mutually opposite sides and have on their surfaces facing the clamping jaws 19 likewise a concave shape adapted to the shape of the clamping jaws. Such a muffle 5 is shown at the right in FIG. 4. Instead of lugs 20, recesses are conversely possible in the muffle itself. Another possibility for connecting the muffle 5 with the pick-off device 13 consists in that the distal ends of the clamping levers 18 be provided with hooks (not shown) that can be introduced or locked in corresponding eyelets 21 of the muffle 5. A muffle having eyelets 21 as reciprocal members is shown at the left in FIG. 4.

Since muffles of different sizes or diameters are generally used, it is necessary for an economical manufacture and thus for casting in continuously consecutive working operations that care be adequately taken to assure that the longitudinal central plane of the reciprocal members 20 of the muffles 5 also lie at the same level so that the pick-off device 13 can reliably grip the muffles to be removed from the preheater furnace 1.

Figure 4:
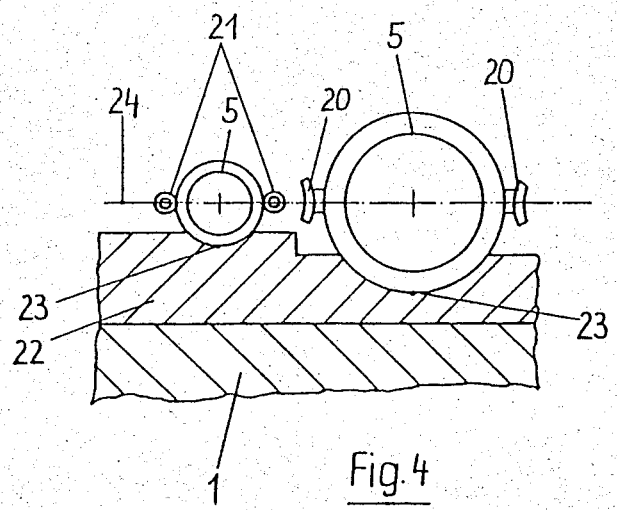
FIG. 4 is a sectional enlargement of one part of the preheater furnace.

For this purpose there is now provided within the preheater furnace 1 an insert 22 that can be fixed or removable. The insert 22 has bearing surfaces 23 at different heights in a manner such that the muffles laid on the bearing surfaces 23 be at an equal level. In FIG. 4 the level is designated by reference character 24.

Figure 2:
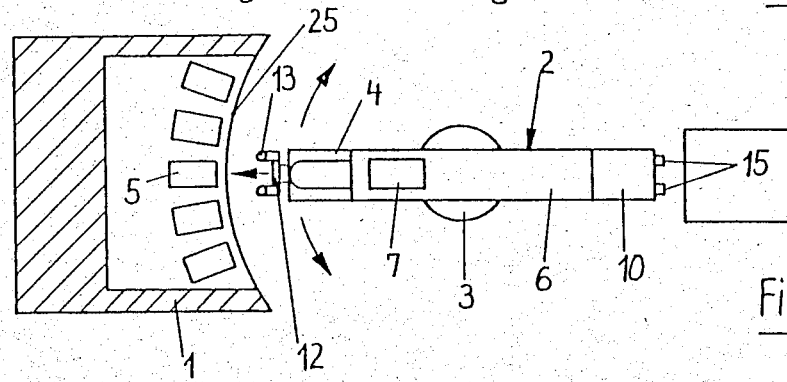
FIG. 2 is a top view of the apparatus according to the invention.

In order that all movements of the manipulator arm 12 be almost constant and that it will have to carry out only a rectilinear movement on the same level, the preheater furnace 1 is provided in the forward side with a curve-like opening 25 (see FIG. 2). The radius of the opening 25 here must have its middle point at least approximately on the axis of the drive mechanism 3 and thus of the centrifugal arm 2. The inserts 22 likewise have to be aligned with their bearing surfaces 23 for the muffles 5. In this case said parts are aligned exactly radially to the axis of rotation of the centrifugal arm 2.

On the end having the counterweight 10, the centrifugal arm 2 is provided with compressed air connections 15. Via the compressed air connections 15, which are readily detachably connected with a source of compressed air not shown, the interior 6 of the centrifugal arm 2 can be supplied with compressed air. For a vacuum die casting a vacuum can likewise be produced in the interior. The pneumatic cylinders are also supplied with compressed air via the compressed air connections. Instead of situating the compressed air connections on the rear end of the centrifugal arm, compressed air can also be passed via the driving shaft of the centrifugal arm. This can be effected here, for instance, via pneumatic rotary transmitters known already. The apparatus according to the invention now functions as follows:

From the supply cartridge 7, a premeasured amount of material for a false tooth is introduced in the melt receptacle 4. The resistance heater is then actuated and as soon as the gold is molten, a preheated muffle 5 is removed from the preheater furnace 1 and connected with the melt receptacle 4 by correspondingly actuating the manipulator arm 12 or the pneumatic cylinders 14 and 16. Compressed air is then introduced into the interior 6 of the centrifugal arm 2 via the compressed air connections 15, the connection with the source of compressed air is released and the centrifugal arm 2 is shifted to rotational movement by the drive mechanism 3. In this manner the fused gold is transmitted very quickly at high speed and under pressure from the melt receptacle 4 precisely into the muffle 5.

The centrifugal arm 2 is decelerated and the connection of the muffle 5 to the melt receptacle 4 is released, allowing the muffle to fall into an underlying receiving drum.

A new premeasured amount of material for a false tooth is then introduced into the melt receptacle 4, the centrifugal arm is rotated one cycle so that the manipulator arm 12 can remove the next muffle 5 from the preheater furnace 1 by a simple rectilinear movement on the same level, and the operation is repeated until there is no more material for false teeth in the supply cartridge.

I claim:

1. An apparatus for casting materials for false teeth, especially gold, from a melt receptacle into a muffle preheated in a preheater furnace, wherein said melt receptacle together with the muffle attached thereto by a connecting means is disposed on a centrifugal arm of a centrifugal device that rotates during a casting operation, wherein said preheater furnace (1) and said connecting means (9,13) are situated upon a common structural unit (8) so close to each other that to convey said muffle (5) and fasten it on said connecting means there is provided an actuable manipulator arm (12) which carries out only one shifting movement in one plane and which engages said muffle.

2. An apparatus according to claim 1, wherein said manipulator arm (12) is fastened to said centrifugal arm (2) and is actuatable by one or more pneumatic cylinders (14,16).

3. An apparatus according to claim 2, wherein said centrifugal arm (2) is provided with compressed air connections (15) for supplying compressed air to said pneumatic cylinders (14,16).

4. An apparatus according to claim 2, wherein said centrifugal arm (2) is constructed, at least in the area in which said melt receptacle (4) is situated in the interior, as a tightly lockable arm, said muffle (5) being tightly connectable with said melt receptacle (4).

5. An apparatus according to claim 1 wherein for the conveyance of muffles (5) of different diameters into said preheated furnace (1) there is disposed an insert (22) having at different heights bearing surfaces (23) for said muffles (5), all longitudinal axes of said muffles (5) being on the same level (24).

6. An apparatus according to claim 5, wherein said bearing surfaces (23) are on a sector having its central point at least approximately in the area of the axis of rotation of the centrifugal arm (2).

7. An apparatus according to claim 2, wherein one pneumatic cylinder (14) is provided for the horizontal movement of said manipulator arm (12) and another pneumatic cylinder (16) engages a pick-off device (13) for said muffle (5).

8. An apparatus according to claim 7 wherein said pick-off device (13) is shaped like a pair of tongs having two clamping levers (18) between which the double-acting pneumatic cylinder (16) engages for actuating said two clamping levers.

9. An apparatus according to claim 8 wherein said clamping levers (18) are provided with retaining member (19) which interact with reciprocal members (20) situated on said muffle (5) to be conveyed.

10. An apparatus according to claim 9, wherein said retaining members are clamping jaws (19) and said reciprocal members on the outer contour of said clamping jaws are adapted lugs or recesses (20) in the peripheral wall of said muffle (5).

11. An apparatus according to claim 9, wherein said retaining members are provided with hooks that can be introduced into said reciprocal members constructed as eyelets (21) on said muffle.

* * * * *